United States Patent [19]

Bauer et al.

[11] Patent Number: 4,608,068
[45] Date of Patent: Aug. 26, 1986

[54] RECOVERY OF $C_{3+}$ HYDROCARBONS

[75] Inventors: Heinz Bauer, Neuried; Aldo Belloni, Puchheim, both of Fed. Rep. of Germany

[73] Assignee: Linde Aktiengesellschaft, Wiesbaden, Fed. Rep. of Germany

[21] Appl. No.: 709,742

[22] Filed: Mar. 8, 1985

[30] Foreign Application Priority Data

Mar. 9, 1984 [DE] Fed. Rep. of Germany ....... 3408760

[51] Int. Cl.⁴ ............................................. A25J 3/02
[52] U.S. Cl. ........................................ 62/18; 62/31; 62/34; 62/39
[58] Field of Search ............... 62/38, 39, 31, 34, 18, 62/24, 29, 30

[56] References Cited

U.S. PATENT DOCUMENTS 4,478,621 10/1984 Fabian ................................. 62/34

*Primary Examiner*—Frank Sever

*Attorney, Agent, or Firm*—Millen & White

[57] ABSTRACT

In the recovery of $C_{3+}$ hydrocarbons from a feed stream containing hydrogen and $C_1$ to at least $C_5$ hydrocarbons, e.g., a refinery waste gas, comprising cooling and partially condensing the feed stream; separating the partially condensed feed stream into a liquid fraction and a gaseous fraction; expanding the gaseous fraction, and fractionating the liquid fraction in a rectification column to obtain product stream consisting essentially of $C_{3+}$ hydrocarbons and a residual gas stream product containing predominantly $C_{2-}$ hydrocarbons, one improvement comprises passing (a) the gaseous fraction prior to expansion; (b) the liquid fraction prior to rectification; and (c) the gaseous fraction after expansion, in indirect heat exchanger relationship with the feed stream to be cooled. Other improvements comprise separate removal of $C_1$ and $C_2$ fractions from the hydrogen gas; the use of a $C_{5+}$ fraction as a feed to the rectification column and/or as a scrubbing liquid for separating the partially condensed feed stream.

23 Claims, 6 Drawing Figures

RECOVERY OF $C_{3+}$ HYDROCARBONS

BACKGROUND OF THE INVENTION

This invention relates to the recovery of $C_{3+}$ hydrocarbons from a feed stream generally containing, as essential components, hydrogen as well as $C_1$ to at least $C_5$ hydrocarbons. Conventionally, such a feed stream is cooled to provide a liquid fraction and a gaseous fraction. The liquid fraction is then fractionated by rectification into a product stream containing essentially $C_{3+}$ hydrocarbons and a residual gas stream containing predominantly $C_{2-}$ hydrocarbons.

Such processes are used primarily for the separation of propane (optionally propylene and higher hydrocarbons as well) from refinery waste gases. The processing of refinery waste gases has become of interest lately from an economics viewpoint, since the market prices for LPG ($C_3/C_4$ hydrocarbon mixture) have risen, while the demand for vacuum residues as well as heavy oil has decreased. For this reason, the poorly marketable heavy products are burned to cover internal fuel needs whereas readily marketable $C_{3+}$ hydrocarbons are separated from the waste gas.

A process of the above-discussed type has been described (*Oil and Gas Journal*, May 10, 1982, pp. 127-313) wherein a refinery waste gas with the aforedescribed composition is first compressed to the required process pressure and, after separation of water, is cooled and partially condensed. The condensate is introduced into a rectification column wherein a liquid $C_3$ hydrocarbon fraction and a gaseous $C_{2-}$ hydrocarbon fraction are obtained. The gas phase from the partial condensation step is expanded in a turbo-expander to result in a two phase fluid and said fluid is introduced into the rectification column as reflux.

Because the two phase fluid is employed as reflux, several disadvantages occur. On the one hand, the increase in concentration of lighter components in the rectification column requires the rectification column to be operated at relatively low temperatures and accordingly consumes a large amount of refrigeration energy. On the other hand, because the light proportion introduced into the separating column is a two-phase mixture, the expansion of the gas into the liquid-vapor range must be performed in an especially high-quality and expensive turbo-expansion device designed for this purpose.

SUMMARY OF THE INVENTION

An object of one aspect of this invention is to provide an improved process of the above-discussed type.

An object of another aspect of the invention is to provide associated apparatus for the improved process.

Upon further study of the specification and appended claims, further objects and advantages of this invention will become apparent to those skilled in the art.

To attain these objects, the gaseous fraction prior to expansion, the liquid fraction prior to rectification, and the gaseous fraction after expansion are all brought into indirect heat exchange relationship with the feed stream to be cooled.

In the process of this invention, the cold produced by the gas phase expansion is not used, as heretofore, for the formation of reflux liquid for rectification, but rather for partially condensing the feed stream. Therefore, it is no longer necessary to pass the lighter components from the feed stream into the rectification column. Likewise, it is unnecessary to produce a two-phase fluid mixture during the expansion step. Thus, according to one feature of this invention, the gaseous stream to be expanded is preheated in order to avoid expansion into the liquid-vapor region as well as to transfer its cold value to the system. Also, by virtue of the present invention, the feed condensate produced by means of expansion cold, is obtained at a temperature level lower than that required for the subsequent rectification. The excess cold is utilized, according to another feature of this invention, for cooling the feed stream.

By one or more, and in particular the combination of the features of this invention, a number of advantages are obtained. By the elimination of the light components of the feed stream (especially hydrogen, as well as $C_1$ and $C_2$ hydrocarbons) in the separating column, the rectification can be conducted at a higher temperature level. This means that, with the usual compositions of the mixture to be rectified, simple and inexpensive external-cold cycles in the temperature range of above about $-50°$ C., typically $-35°$ to $-40°$ C., can be used for partially condensing the overhead gas in order to provide reflux. Furthermore, since no condensate is formed during expansion, less expensive expansion devices can be utilized. Finally, the heating of the three cold process streams in indirect heat exchange with the feed stream to be cooled results in very small temperature differences at the cold end of the heat exchanger so that the heat exchange losses are small.

It is also advantageous according to another preferred feature of the process of this invention to cool the feed gas by external refrigeration and cold fractionation products. The resultant partial condensate of the feed (i.e. the liquid fraction) is preferably heated at least up to the temperature of the coldest external cold level and the resultant gaseous fraction to be expaded has to be heated by about 5° C. to 25° C. The expanded gaseous fraction preferably will be heated no more than up to the coldest external cold level.

According to another preferred feature of the process of this invention, the liquid fraction is heated to at least the same temperature level as the gaseous stream obtained during rectification.

According to a preferred further aspect of the process of this invention, at least a portion of the gaseous fraction is utilized, after expansion, as regenerating gas for a prepurification process, e.g., to regenerate upstream prepurification adsorbers used to remove $H_2O$ from the feed gas.

According to another preferred embodiment, the gaseous fraction to be expanded, prior to heating, is further condensed to liquify $C_1$ and $C_2$ hydrocarbons in order to obtain hydrogen of high purity.

The rectification step is particularly efficiently conducted if the feed stream has a relatively high hydrogen proportion, preferably on the order of magnitude of 50-90% by volume. In any case, the amount of hydrogen should be sufficient for producing the required refrigeration during expansion so that the hydrogen can be recovered. A portion of the expanded $H_2$ is preferably added to the condensed light hydrocarbons to improve their evaporation characteristics.

For many uses, further fractionation of the $C_{3+}$ hydrocarbon product is desirable, especially separation between a $C_3/C_4$ hydrocarbon mixture and $C_{5+}$ hydrocarbons. For this purpose, in accordance with a preferred embodiment of the process of this invention, prior to formation of the liquid fraction and the gaseous fraction, the major portion of the $C_{5+}$ hydrocarbons is separated from the feed stream, together with a small quantity of $C_4$ hydrocarbons. Separation is advantageously accomplished by partial condensation at a temperature lying above the temperature at which the above-mentioned liquid and gaseous fractions are formed. By effecting such an upstream separation, the mixture fed to the rectification column is substantially free of $C_{5+}$ hydrocarbons. During the subsequent rectification, a $C_3/C_4$ hydrocarbon product stream is obtained.

To increase the yield of $C_3$ and $C_4$ hydrocarbons, according to a still further preferred embodiment, the separated heavy hydrocarbons ($C_{5+}$) are likewise passed to rectification. In particular, the heavy hydrocarbons are introduced into the rectification column below the feed point of the liquid fraction, and a stream containing essentially $C_3$ and $C_4$ hydrocarbons is withdrawn between the two feed points. Accordingly, rectification is performed not only on the liquid fraction but also on the heavy components previously separated from the feed stream. The precise feedpoints of the two streams into the rectification column are determined in correspondence with their differing compositions. Between the two feed points exists a region of maximum $C_3/C_4$ hydrocarbon concentration. At that location, a $C_3/C_4$ hydrocarbon product stream is withdrawn. Additionally, a stream rich in $C_{5+}$ hydrocarbons is obtained in the sump of the column and which contains only a small amount of $C_4$ hydrocarbons.

In a preferred further feature of the process of this invention, the gaseous fraction, after its expansion, is passed to the gas phase part of the phase separator in order to be heat exchanged with the gaseous phase from the phase separation of the feed stream or, respectively, of the stream formed from the feed stream after separation of the $C_{5+}$ hydrocarbons. By virtue the heat exchange, the modified phase-separator employed for phase separation also acts as an enriching means so that the yield is increased. There are no additional operating costs caused thereby.

According to another preferred embodiment of the process of this invention, at least part of the work gained during expansion of the gaseous fraction is utilized for compression of the feed stream and/or for recompression of the expanded gaseous fraction.

According to still another preferred feature of the invention, phase separation of the feed stream, or, respectively, of the stream formed from the feed stream after separating the $C_{5+}$ hydrocarbons is conducted by means of a scrubbing step. In this connection, it is especially advantageous if a scrubbing liquid containing essentially $C_{5+}$ hydrocarbons is utilized. Such a scrubbing liquid can be withdrawn from the sump of the fractionation stage arranged downstream of the rectification column.

Apparatus for conducting the process of this invention comprises a feed conduit for a feed stream, followed by an optional but preferred prepurification stage, a heat exchanger, and phase-separating means the liquid-collecting chamber of the latter being connected with a rectification column, and the gas-collecting chamber being connected with an expansion means, and which is characterized in that the conduits connecting the phase-separating-means liquid chamber and the rectification column, and/or the phase-separating-means gas collecting chamber with the expansion means, and the waste gas conduit from the expansion means, are passed through the heat exchanger.

In a preferred embodiment of the apparatus of this invention, a heat exchanger connected to the outlet of the expansion means is provided in the gas space of the phase-separating means.

In another preferred embodiment of the apparatus of this invention, a scrubbing column is provided as the phase-separating means.

In another preferred embodiment, the expansion means is coupled with a compressor for the feed stream and/or with a recompressor for the waste gas of the expansion device.

BRIEF DESCRIPTION OF THE DRAWINGS

Preferred embodiments of the invention are described in greater detail with reference to the schematic illustrations in the drawings, wherein.

DETAILED DESCRIPTION OF THE DRAWINGS

Figure 1:
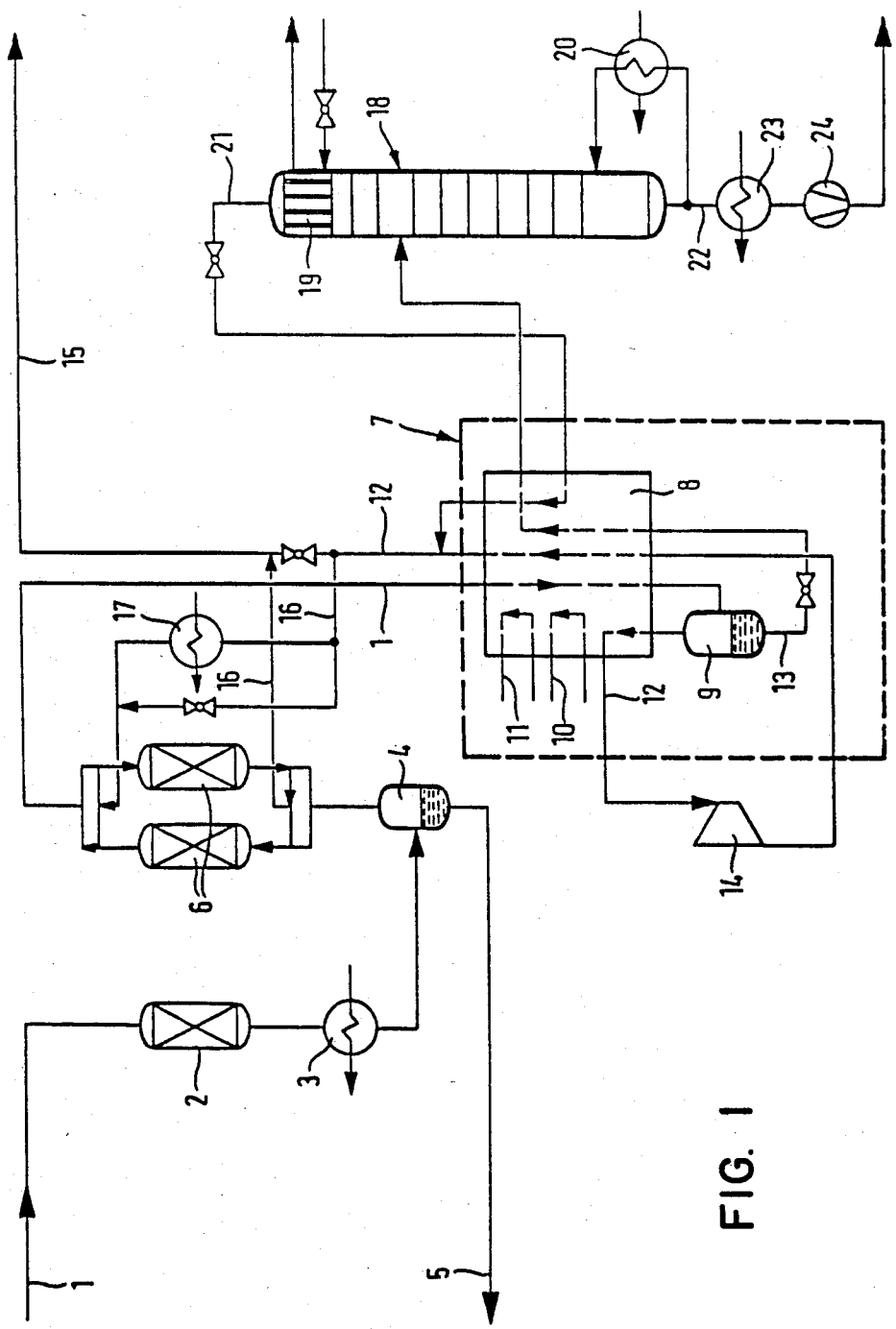
FIG. 1 is a system according to the invention providing for optional prepurification as well.

In the description of the figures, the same reference numerals are utilized for analogous components.

A feed stream 1, which is, for example, a refinery waste gas as obtained in the processing of light crude oil components to gasoline, has a composition of 10–90% hydrogen, $C_1$ to $C_5$ hydrocarbons, water, hydrochloric acid, as well as, in some cases, $C_{5+}$ hydrocarbons and hydrogen sulfide. Its pressure, after a precompression that may be required, amounts to about 15–30 bar; its temperature is at the cooling water temperature level (25°–35° C.) or higher. The feed stream is first conducted through a reactor or adsorber 2 filled with molecular sieves or alumina gel wherein the hydrochloric acid is removed. The feed stream, devoid of hydrochloric acid, is then cooled in a cooler 3 to about 25°–35° C. During this step, a large part of the water contained in the feed stream is condensed out and is separated in a separator 4 and removed via conduit 5. The feed stream is thereafter conducted to a pair of alternatingly operated dryers 6 filled with molecular sieves. In these dryers, final residues of $H_2O$ are removed from the feed stream. The prepurified feed stream leaving the dryers 6 consists essentially of hydrogen are $C_1$ to $C_5$ hydrocarbons, and in some cases further contains $C_{6+}$ hydrocarbons and hydrogen sulfide. This stream is fed to the coldbox 7, shown in dashed lines, the essential components of which are a heat exchanger 8 as well as phase-separating means designed as a phase separator 9. The components 8 and 9 can also be individually insulated, eliminating a coldbox. The prepurified feed stream 1 is cooled to about $-40°$ to $-80°$ C. in heat exchanger 8 in heat exchange with a refrigerant evaporating at one temperature level (10) or optionally at two different temperature levels (10, 11) (preferably $-35°$ to 50° C. as well as, optionally, also 0° to $-20°$ C.), as well as with a series of further process streams which will be described below. During cooling, a portion of the feed stream is condensed, and a two-phase mixture is formed which is introduced into separator 9.

A gaseous fraction 12, containing almost the entire amount of hydrogen present in the feed stream as well as a large portion of the $C_1$ and $C_2$ hydrocarbons, and a liquid fraction 13, consisting essentially of $C_{3+}$ hydrocarbons as well as a small proportion of $C_1$ and $C_2$ hydrocarbons, are withdrawn from the separator 9. The gaseous fraction 12 is conducted through part of heat exchanger 8 and heated therein, in heat exchange with the feed stream 1, to a temperature preferably no higher than that of the refrigerant 10. This fraction leaves the heat exchanger 8 at an intermediate point and is introduced into an expansion turbine 14 wherein it is expanded to about 5-bar. This expansion can optionally take place in two stages with intermediate heating. Heating of the gaseous stream to be expanded in heat exchanger 8 is controlled so that no condensate formation occurs during epxansion. The expansion turbine is optionally coupled with a compressor for the feed stream (not shown).

The expanded gaseous fraction 12, the temperature of which lies about 3°-20° C. preferably about 3° C. to 5° C. below that of the separator 9, is conducted through heat exchanger 8 and heated in heat exchange with the feed stream 1. A partial stream 15 of the gaseous stream 12 is discharged from the installation as fuel gas, whereas another partial stream 16, optionally after having been heated in a heater 17, is utilized as regenerating gas for the dryers 6 during the alternating regenerating cycles. After regeneration, the loaded regenerating gas is introduced into the partial stream 15.

The liquid fraction 13 from phase separator 9 is likewise passed through part of the heat exchanger 8 and is heated in heat exchange with the feed stream 1 to be cooled. Heating takes place preferably up to the temperature level of the warmer refrigeration cycle 11. After it has been heated, the liquid fraction 13 is discharged from the heat exchanger 8 at an intermediate point and introduced into rectification column 18 wherein rectification of the liquid mixture is performed. The column 18 is operated under a pressure of about 10-20 bar, preferably 13-15 bar. In this column, separation is accomplished between the $C_{2-}$ and $C_{3+}$ fraction, it being sufficient to cool the head of the separating column 18 to about $-35°$ to $-50°$ C. This is effected by vaporizing an external refrigerant corresponding to refrigerant 10 in the head condenser 19. A combined refrigeration cycle is thereby employed for heat exchanger 8 and condenser 19.

The sump of the separating column is heated by an external boiler 20, heated, for example, by means of low-pressure steam or hot water.

The products of the rectification comprise: (A) a vapor-phase overhead product 21 consisting essentially of $C_1$ and $C_2$ hydrocarbons with at most 1-3% $C_{3+}$ hydrocarbons (residual gas stream; and (B) a liquid sump fraction 22, consisting essentially of $C_{3+}$ hydrocarbons and at most 1-10% $C_2$ hydrocarbons. The liquid $C_{3+}$ product stream 22 is optionally supercooled in a cooler 23 and brought to the required discharge pressure by means of a pump 24. The gaseous fraction 21 is expanded to a pressure lying above the combustion gas pressure by only a sufficient make-up amount for the pressure losses incurred during the heating and regeneration of the adsorbers. Subsequently, this fraction is introduced in correspondence wtih its temperature, at an intermediate point into the heat exchanger 8 and, after being heated against the feed stream 1 to be cooled, is admixed to the expanded gaseous fraction 12.

Figure 2:
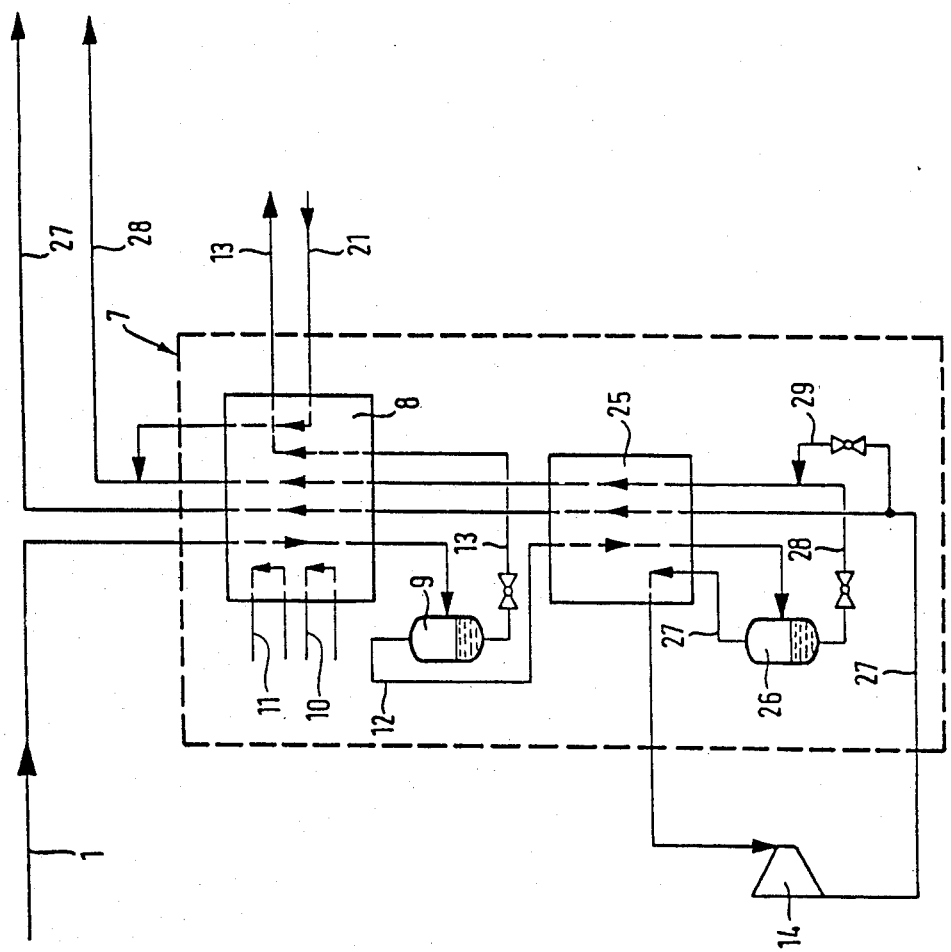
FIG. 2 is a system with additional hydrogen recovery.

In FIG. 2, the prepurification stages as well as the rectification have not been illustrated. In contrast to the system described in FIG. 1, the gaseous fration 12 from separator 9 is not directly expanded in turbine 14 but rather is first introduced into a heat exchanger 25 wherein it is cooled in heat exchange with three cold streams which will be described below. At the cold end of heat exchanger 25, fraction 12 has a temperature of about $-140°$ to $-170°$ C. At this temperature, some of the components contained in fraction 12 condense. In a phase separator 26, the two-phase mixture is then separated into a gaseous phase 27 consisting essentially of hydrogen, and into a liquid phase 28 consisting essentially of $C_1$ and $C_2$ hydrocarbons. The gaseous phase 27 is conducted through part of the heat exchanger 25 and heated in heat exchange with the stream 12 to be cooled, before it is fed into turbine 14. In turbine 14, the gaseous stream 27 is expanded to about 5-15 bar. Preheating of the to-be-expanded stream 27 prevents formation of condensate during expansion.

The expanded gaseous stream 27 is conducted successively through the heat exchangers 25 and 8, during which step it is heated in heat exchange with the streams 12 and 1, respectively, to be cooled.

The liquid phase 28 is likewise passed successively through heat exchangers 25 and 8 where it is heated. Between conduits 27 and 28, upstream of the entrance into heat exchanger 25, a connecting conduit 29 is arranged, through which a certain amount of hydrogen 29 is admixed to $C_1/C_2$ hydrocarbon mixture 28 in order to lower the partial pressure of the hydrocarbons and to permit vaporization at a lower temperature.

The system according to FIG. 2 offers the possibility of obtaining, besides a $C_{3+}$ hydrocarbon fraction, hydrogen as a product as well. This process is practicable from an economical viewpoint only if the hydrogen proportion contained in feed stream 1 is adequate for generating the required cold in turbine 14.

Figure 3:
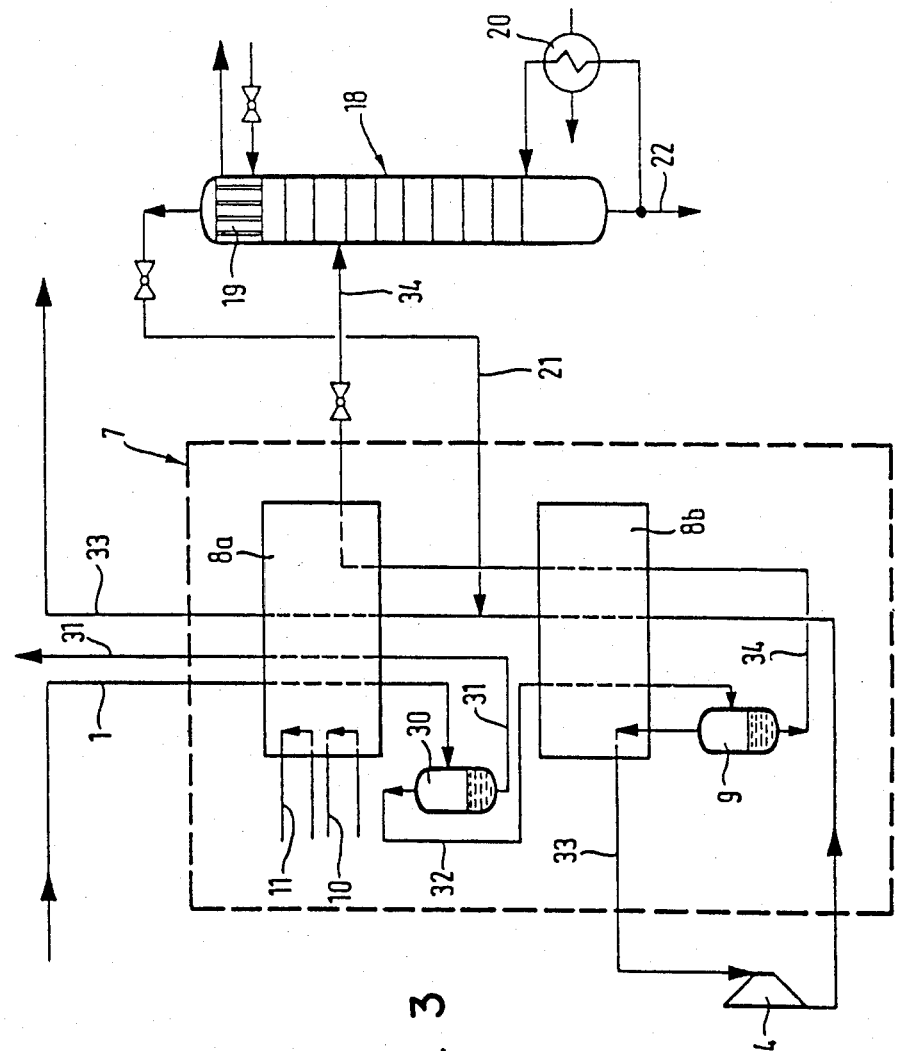
FIGS. 3 and 4 are two embodiments providing for additional $C_{5+}$ separation.

In FIG. 3 there is depicted an embodiment wherein a $C_3/C_4$ hydrocarbon mixture, without a $C_{5+}$ proportion, is obtained as the product. In this process, cooling of the feed stream 1 takes place in two stages, namely in two heat exhangers 8a and 8b. Depending on the size of the exchanger, they can also be integrated, with one heat exchanger body or block being used. After cooling in heat exchanger 8a against external refrigerant, wherein its higher evaporation level (11) or the lower level (10), or both levels together (10, 11) are utilized, depending on the raw gas composition and the pressure, as well as against three streams 31, 33, 34, to be described below, the feed stream 1 has a temperature of about $-10°$ to $-35°$ C. At this temperature, the largest portion of the $C_{5+}$ hydrocarbons is condensed out. The two-phase mixture is introduced into a separator 30 wherein the gaseous phase is separated from the liquid phase. The liquid phase consisting essentially of $C_{5+}$ hydrocarbons as well as $C_3$ and $C_4$ hydrocarbons, is withdrawn via conduit 31 and conducted through heat exchanger 8a wherein it is heated against the feed stream 1.

The gaseous phase, consisting essentially of hydrogen, and also containing $C_1$ to $C_4$ hydrocarbons, is withdrawn via conduit 32 and further cooled in heat exchanger 8b. During this step, a two-phase mixture is formed which is fed into separator phase 9. The gaseous phase 33, consisting essentially of hydrogen and containing $C_1$ and $C_2$ hydrocarbons, is introduced, after being heated in heat exchanger 8b, into the turbine 14 wherein it is expanded. The heating in heat exchanger 8b is conducted to such an extent that no condensate formation occurs during expansion.

The expanded gaseous stream 33 is conducted through heat exchangers 8b and 8a wherein it is heated against the feed stream 1 and stream 32, respectively.

The liquid fraction 34 from separator 9, consisting essentially of $C_3$ and $C_4$ hydrocarbons, as well as $C_1$ and $C_2$ hydrocarbons, is heated in heat exchanger 8b and further heated in heat exchanger 8a up to about the temperature level of the refrigerant 10. The stream is withdrawn from heat exchanger 8a at an intermediate point and introduced into the separating column 18. In the latter, the rectification described with reference to FIG. 1 is conducted, except that the sump product 22 is substantially free of $C_{5+}$ hydrocarbons, e.g., preferably less than about 0.5 volume % $C_{5+}$.

Figure 4:
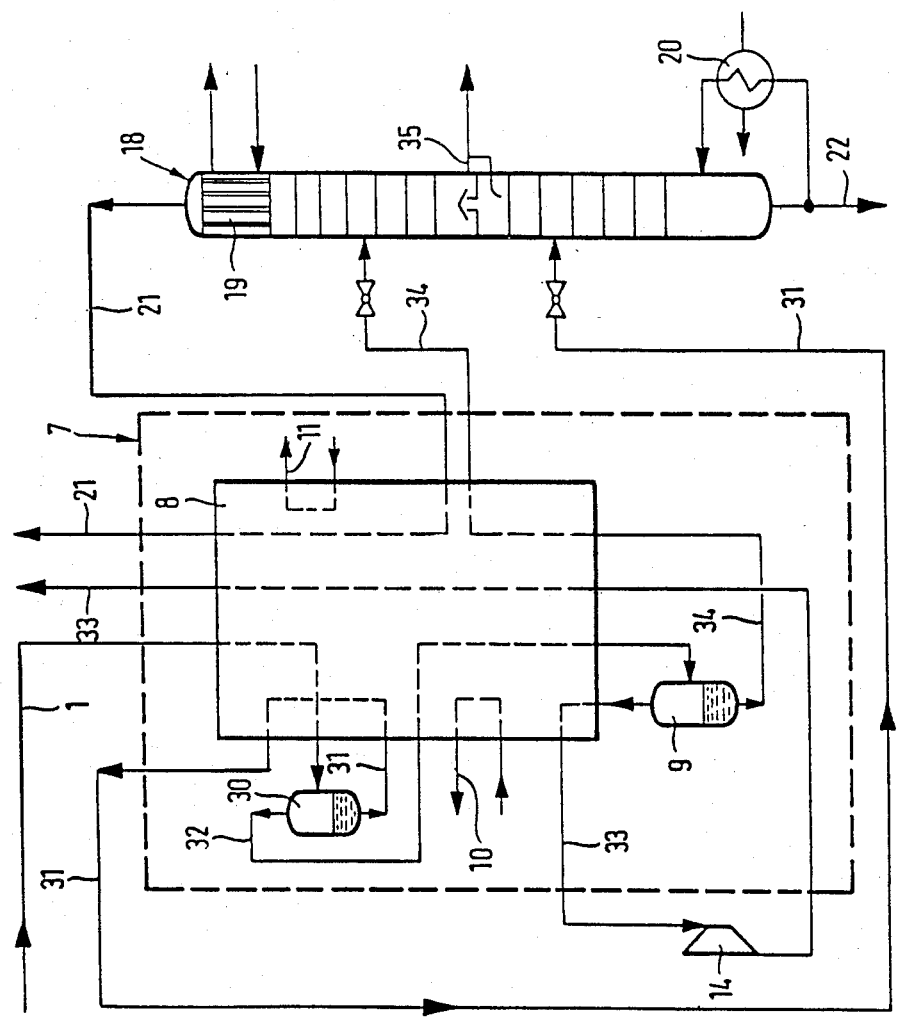

The process according to FIG. 3 has, however, the drawback that during the separation of $C_{5+}$ hydrocarbons in separator 30, performed as a preceding step, a significant proportion of $C_3$ and $C_4$ hydrocarbons is separated together with the condensate. An embodiment of the process as will now be described in connection with FIG. 4 makes it possible to achieve a higher yield of $C_3$ and $C_4$ hydrocarbons.

The dried feed stream 1 is cooled, analogously to the process illustrated in FIG. 3, only to a temperature at which the $C_{5+}$ hydrocarbons are condensed. The two-phase mixture, withdrawn from the heat exchanger 8 at an intermediate point, is introduced into separator 30 wherein phase separation is performed. The gaseous phase 32 is returned into heat exchanger 8 at an intermediate point and discharged therefrom at the cold end. The liquid phase 31, in contrast thereto, is introduced, after having been heated in part of heat exchanger 8, into the separating column 18. The feed point for this is below the location where the fraction 34 from separator 9 is introduced into the separating colun 18.

The rectification column 18 has a larger number of plates (about 20 to 40 theoretical plates) than the rectification column in the process according to FIG. 3 (about 10 to 25 theoretical plates). The column exhibits bits a discharge conduit 35 between the two feed points for streams 31 and 34. In this region there is a maximum concentration of $C_3$ and $C_4$ hydrocarbons.

Via conduit 22, a liquid consisting essentially of $C_{5+}$ is withdrawn from the sump of the separating column 18. A gaseous fraction is discharged from the head of separating column 18 via conduit 21, containing in essence $C_1$ and $C_2$ hydrocarbons.

In contrast to the system according to FIG. 3, the heavy components separated in separator 30 are, in this embodiment, likewise introduced into the rectification column. In this way, with a relatively low expenditure, a very high yield of $C_3$ and $C_4$ hydrocarbons can be achieved.

Figure 5:
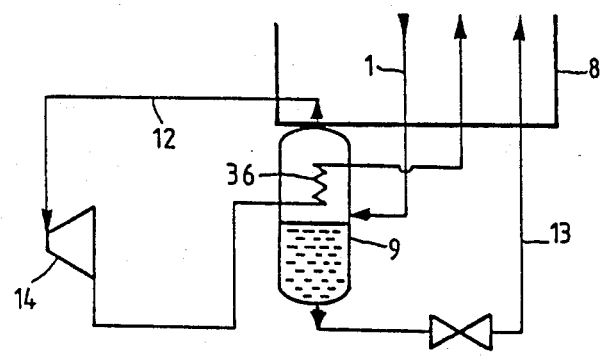
FIG. 5 shows a detail of a preferred embodiment of a separating device incorporated in this invention.

In the detailed embodiment illustrated in FIG. 5, a heat exchanger 36 is provided in the gas space of separator 9 and is connected to the exhaust side of turbine 14. By virtue of the heat exchanger 36, the separator 9 operates like an enrichment column so that the yield in phase separation is increased. The heat exchanger 36 can be included in the system of FIG. 1 wherein the feed stream 1 is fed into the separator 9, as well as in FIG. 3 or FIG. 4 wherein a stream 32, formed from the feed stream after separation of the $C_{5+}$ hydrocarbons is introduced into phase separator 9.

Figure 6:
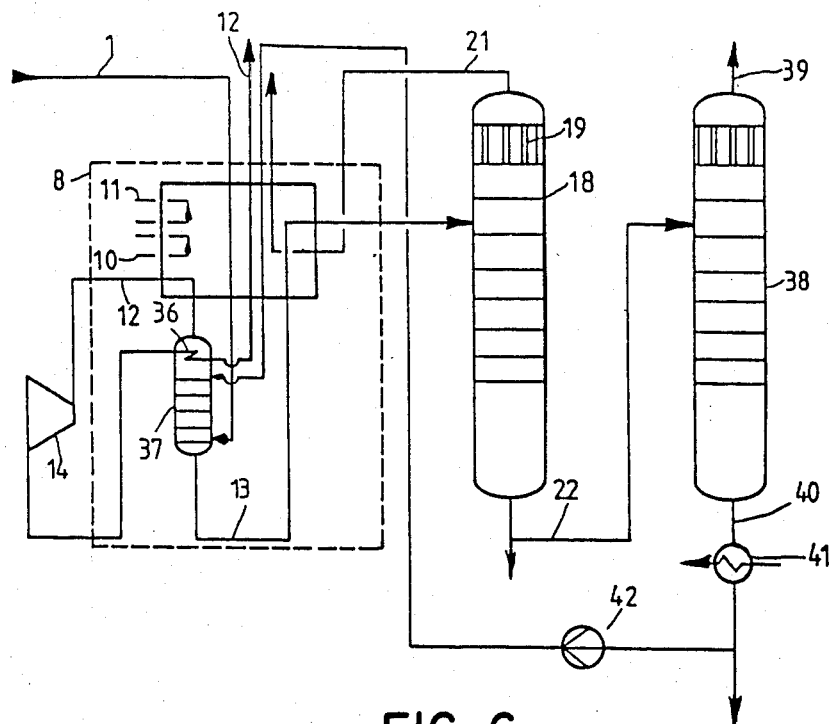
FIG. 6 is another preferred embodiment of the invention including a downstream further rectification column and a scrubber used as a phase separator.

In the embodiment of FIG. 6, phase separation of the feed stream 1 is conducted in a scrubbing column 37. The gaseous fraction 12 withdrawn overhead is engine-expanded in the turbine 14; the expanded gaseous stream is utilized in the heat exchanger 36 for cooling the head of the scrubbing column 37. The liquid sump fraction from scrubbing column 37 is fed via conduit 13 into the rectification column 18. The $C_{3+}$ fraction 22, withdrawn from the sump of rectification column 18, is introduced into another rectification column 38 wherein separation is effected into a $C_3/C_4$ fraction, withdrawn via conduit 39 from the head of rectification column 38, and into a $C_{5+}$ fraction, discharged via a conduit 40 from the sump of the rectifying column 38. The $C_{5+}$ fraction is cooled in a cooler 41 and, by means of a pump 42, is fed as reflux into the scrubbing column 37.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the recovery of $C_{3+}$ hydrocarbins from a feed stream containing hydrogen and $C_1$ to at least $C_5$ hydrocarbons, comprising cooling and partially condensing the feed stream; separating the partially condensed feed stream into a liquid fraction and a gaseous fraction; expanding the gaseous fraction to produce a colder fluid, and fractionating the liquid fraction in a rectification column to obtain a product stream consisting essentially of $C_{3+}$ hydrocarbons and a residual gas stream product containing perdominantly $C_{2-}$ hydrocarbons, the improvement comprising passing: (a) the gaseous fraction prior to expansion, (b) the liquid fraction, prior to rectification, and (c) the gaseous fraction after expansion, all in indirect heat exchange relationship with the feed stream to be cooled wherein said rectification is conducted at a temperature sufficiently high to enable an external-refrigeration cycle having a temperature above about $-50°$ C. to be employed for partially condensing the overhead gas to provide reflux for the rectification column.

2. A process according to claim 1, wherein said feed stream to-be-cooled in further passes in indirect heat relationship with external cooling media, and said liquid fraction of the feed, during said indirect heat exchange, of the feed stream to-be-cooled is heated at least up to the temperature of the coldest external cooling level, and the gaseous fraction to be expanded is heated to a lower temperature than that of said liquid fraction.

3. A process according to claim 1 wherein the liquid fraction during said indirect heat exchange is heated to at least the same temperature level as the residual gas stream product obtained during rectification.

4. A process according to claim 1 further comprising prepurifying the feed stream in cyclical adsorbers and regenerating said adsorbers with at least a portion of said gaseous fraction, after the expansion thereof.

5. A process according to claim 1 further comprising partially condensing the gaseous fraction to be expanded, prior to heating thereof, to separate $C_1$ and $C_2$ hydrocarbons.

6. A process according to claim 1 further comprising, prior to formation of the liquid fraction and the gaseous fraction, separating the major portion of $C_{5+}$ hydrocarbons from the feed stream.

7. A process according to claim 6, further comprising feeding the separated, $C_{5+}$ hydrocarbons into said rectification column at a point below the feed point of the liquid fraction; and withdrawing a stream consisting essentially of $C_3$ and $C_4$ hydrocarbons from the column at a point between the two feed points.

8. A process according to claim 6 further comprising passing the gaseous fraction, after expansion thereof, into indirect heat exchange relationship with the gaseous phase directly withdrawn from the phase separation of the feed stream and/or of the stream formed from the feed stream after separation of the $C_{5+}$ hydrocarbons.

9. A process according to claim 6 wherein the separation of the partially condensed feed stream or, respectively, of the feed stream formed from the feed stream after separation of the $C_{5+}$ hydrocarbons is conducted by scrubbing the partial condensate with a scrubbing liquid.

10. A process according to claim 9, characterized in that a scrubbing liquid containing essentially $C_{5+}$ hydrocarbons is utilized for the scrubbing step.

11. A process according to claim 1 further comprising passing the gaseous fraction, after expansion thereof, into indirect heat exchange relationship with the gaseous phase directly withdrawn from the phase separation of the feed stream.

12. A process according to claim 1 wherein said expansion is conducted in a turboexpander, and employing at least part of the work gained during said expansion of the gaseous fraction of compress the feed stream and/or for recompress the expanded gaseous fraction.

13. A process according to claim 1 wherein the separation of the partially condensed feed stream is conducted by scrubbing the partial condensate with a scrubbing liquid.

14. A process according to claim 1, characterized in that a scrubbing liquid containing essentially $C_{5+}$ hydrocarbons is utilized for the scrubbing step.

15. A process according to claim 10, further comprising fractionating said liquid fraction consisting essentially of $C_{3+}$ hydrocarbons in a fractionation stage arranged downstream of the rectification step, and withdrawing from said downstream fractionation stage a $C_{5+}$ stream to be used as the scrubbing liquid.

16. A process according to claim 1 wherein the colder fluid produced by the gas phase expansion is a single phase gaseous fluid.

17. A process according to claim 16, said colder fluid being employed not for the formation of reflux liquid for the rectification column but rather for partially condensing the feed stream.

18. A process according to claim 1, said colder fluid being employed not for the formation of reflux liquid for the rectification column but rather for partially condensing the feed stream.

19. A process according to claim 1, further comprising conducting said rectification at a temperature sufficiently high to enable an external-refrigeration cycle having a temperature above about $-50°$ C. to be employed for partially condensing the overhead gas to provide reflux for the rectification column.

20. An apparatus suitable for separating a refinery waste gas, comprising a feed conduit for the feed stream integrated with prepurification means, a heat exchanger, and phase-seperating means, the liquid-collecting chamber of the latter being connected to a rectification column, and the gas-collecting chamber of the phase separating means being connected to expansion means, wherein the conduits connecting the phase-separating means (9) and the rectification column (18) or, the expansion means (14), are passed through the heat exchanger (8), the improvement which comprises a heat exchanger (36) being connected to the outlet of the expansion device (14) and being disposed in the gas space of the phase-separating means (9), said heat exchanger (36) being designated so as to permit said rectification to be conducted at a temperature sufficiently high to enable an external-refrigeration cycle having a temperature above about $-50°$ C. to be employed for partially condensing the overhead gas to provide reflux for the rectification column.

21. Apparatus according to claim 20, wherein said phase-separating means (9) comprises a scrubbing column (37).

22. An apparatus according to claim 16, further comprising a feed conduit for the feed stream integrated with prepurification means, a heat exchanger, and phase-separating means, the liquid-collecting chamber of the latter being connected to a rectification column, and the gas-collecting chamber of the pahse separating means being connected to expansion means, wherein the conduits connecting the phase-separating means (9) and the rectification column (18) or, the expansion means (14), are passed through the heat exchanger (8), the improvement wherein said phase-separating means (9) comprises a scrubbing column (37).

23. Apparatus according to claim 20, said expansion means (14) being coupled with a compressor for the feed stream (1) and/or with a recompressor for the waste gas of the expansion device (14).

* * * * *